(12) United States Patent
Kim et al.

(10) Patent No.: US 11,813,380 B2
(45) Date of Patent: Nov. 14, 2023

(54) PHOTOCATALYTIC DEVICE AND AIR CONDITIONER INCLUDING SAME

(71) Applicant: Hanon Systems, Daejeon (KR)

(72) Inventors: Jae Ho Kim, Daejeon (KR); Ki Hong Kim, Daejeon (KR); Ji-Yong Park, Daejeon (KR)

(73) Assignee: Hanon Systems, Daejeon (KR)

( * ) Notice: Subject to any disclaimer, the term of this patent is extended or adjusted under 35 U.S.C. 154(b) by 173 days.

(21) Appl. No.: 16/494,602

(22) PCT Filed: Oct. 16, 2018

(86) PCT No.: PCT/KR2018/012162
§ 371 (c)(1),
(2) Date: Sep. 16, 2019

(87) PCT Pub. No.: WO2019/132201
PCT Pub. Date: Jul. 4, 2019

(65) Prior Publication Data
US 2020/0324013 A1   Oct. 15, 2020

(30) Foreign Application Priority Data
Dec. 26, 2017   (KR) .......................... 10-2017-0179039

(51) Int. Cl.
*A61L 9/20*   (2006.01)
*B60H 1/00*   (2006.01)
*B60H 3/00*   (2006.01)
*B60H 3/06*   (2006.01)

(52) U.S. Cl.
CPC .......... *A61L 9/205* (2013.01); *B60H 1/00521* (2013.01); *B60H 3/0078* (2013.01); *A61L 2209/14* (2013.01); *B60H 2003/0675* (2013.01)

(58) Field of Classification Search
CPC ........................... A61L 9/205; B60H 1/00521
See application file for complete search history.

(56) References Cited

U.S. PATENT DOCUMENTS

| | | | | |
|---|---|---|---|---|
| 2015/0064069 | A1* | 3/2015 | Yi | ............................. A61L 9/20 422/121 |
| 2016/0325606 | A1* | 11/2016 | Kim | ........................ A61L 9/205 |
| 2019/0321502 | A1* | 10/2019 | Kim | ........................ A61L 9/205 |

FOREIGN PATENT DOCUMENTS

| | | |
|---|---|---|
| JP | 9-940 A | 1/1997 |
| JP | 2000-255257 A | 9/2000 |
| JP | 2012-125756 A | 7/2012 |
| KR | 10-0754014 B1 | 9/2007 |
| KR | 20150087496 A | 7/2015 |
| KR | 10-2016-0035818 A | 4/2016 |
| KR | 20160068076 A | 6/2016 |

* cited by examiner

*Primary Examiner* — Kevin Joyner
(74) *Attorney, Agent, or Firm* — Norton Rose Fulbright US LLP; James R. Crawford

(57) ABSTRACT

The present invention relates to a photocatalytic device and a vehicle air conditioner including the same and, more specifically, to a photocatalytic device and a vehicle air conditioner including the same, and compared with a conventional photocatalytic device, the photocatalytic device readily protects, from external contaminants, electronic elements of a substrate at which a light source for emitting ultraviolet light is provided, and increases structural stability by changing a method for connecting the substrate and a connector with each other.

18 Claims, 7 Drawing Sheets

PHOTOCATALYTIC DEVICE AND AIR CONDITIONER INCLUDING SAME

This application is a national phase under 35 U.S.C. § 371 of International Application No. PCT/KR2018/012162 filed Oct. 16, 2018, which claims the benefit of priority from Korean Patent Application 10-2017-0179039 filed on Dec. 26, 2017, which is hereby incorporated by reference in its entirety.

TECHNICAL FIELD

The present invention relates to a photocatalytic device and an air conditioner including the same, and more particularly, to a photocatalytic device with an increased structural stability in comparison to that of a conventional photocatalytic device, and an air conditioner including the same.

BACKGROUND ART

A vehicle air conditioner is a device for cooling or heating an interior of a vehicle by introducing air from outside the vehicle into the interior of the vehicle, or heating or cooling air in a process of circulating air in the interior of the vehicle. The vehicle air conditioner includes an evaporator for cooling and a heater core for heating, the evaporator and the heater core being provided inside an air conditioner case, and is configured to selectively blow, to each portion of the interior of the vehicle, air cooled by the evaporator or heated by the heater core, by using a door for switching a blowing mode.

Meanwhile, as a vehicle distribution rate continuously increases and a time during which a user stays in a vehicle increases, a study for maintaining comfortability of air inside a vehicle has been continuously conducted. However, since an interior of a vehicle is small and closed, it is easily contaminated, and the contamination of the interior of the vehicle has become severe due to fine dust and various contaminants in the city. Accordingly, an air purification device for a vehicle, which purifies air in an interior of a vehicle, has been developed and used recently.

There may be various types of air purification devices for a vehicle and a photocatalyst filter is also one of the air purification devices for a vehicle. The photocatalyst filter is an air purification device which irradiates a photocatalyst with ultraviolet rays such that a chemical reaction is caused to produce active oxygen, and the active oxygen removes an odor. Examples of an air purification device for a vehicle using the conventional photocatalyst filter include Korean Patent Laid-Open Publication No. 10-2017-0008503 (Hereinafter, referred to as Prior Art 1) filed by the present applicant.

FIG. 1 is an exploded perspective view of a conventional photocatalyst filter 1 used in a vehicle air conditioner.

As illustrated in FIG. 1, in the conventional photocatalyst filter 1, a light source portion 30 and a catalyst portion 40 are positioned between a first case 10 and a second case 20.

The light source portion 30 irradiates the catalyst portion 40 with light and may include a substrate 31 and a light source 32 which is formed on an upper surface of the substrate 31 and irradiates the catalyst portion 40 with ultraviolet rays. When the light source 32 irradiates the catalyst portion 40 with ultraviolet rays, the catalyst portion 40 produces a photocatalytic reaction by the ultraviolet rays emitted from the light source 32 to produce a hydroxyl radical, such that contaminants introduced into the air conditioner and fungi and an order in an evaporator provided in the air conditioner are removed by oxidation of the produced hydroxyl radical.

A fixing member 11 formed in the first case 10 is used to couple the photocatalyst filter 1 to the air conditioner. In order to perform purification using the photocatalytic reaction in the photocatalyst filter 1, there is a need to make a surface opposite to a surface irradiated with light from the light source 32 face the inside of the air conditioner. In this case, various electronic elements formed on one surface of the substrate 31 are exposed to contaminants such as dust, such that a life of the photocatalyst filter is shortened, which is problematic.

DISCLOSURE

Technical Problem

An object of the present invention is to provide a photocatalytic device and an air conditioner including the same which may protect electronic elements of a printed circuit board used for a photocatalyst filter, and at the same time, may perform air purification through a photocatalytic reaction, the air purification being an original purpose of the photocatalytic filter, thereby enabling an increase in durability and life of the photocatalyst filter.

Technical Solution

In one general aspect, a photocatalytic device includes: a body 100; a light source portion 200 including a light source 210 and a substrate 220 and fixed to the body 100, the substrate 220 having one surface to which the light source 210 is fixed and the other surface on which electronic elements are disposed; and a catalyst portion 300 fixed to the body 100 to face the light source 210 and producing a photocatalytic reaction by light emitted from the light source 210 to generate a hydroxyl radical.

The body 100 may include an upper body 110 and a lower body 120 coupled to each other, and the light source portion 200 and the catalyst portion 300 may be positioned between the upper body 110 and the lower body 120.

The body 100 may include a sealing portion 113 protruding from one surface of the body 100 toward the light source portion 200 to seal the other surface of the substrate 220.

The sealing portion 113 may protrude along an outer edge of the substrate 220.

The substrate 220 may be fixed to the body 100 in a state of being fixed to a connector 221 formed at one side of the other surface of the substrate 220.

The body 100 may include a horizontal direction fixing member 115 protruding from one surface of the body 100 facing the catalyst portion 300 toward the catalyst portion 300 and being in contact with a side surface of an end portion of the catalyst portion 300 to fix the catalyst portion 300.

The catalyst portion 300 may be formed to have a polygonal shape, and the horizontal direction fixing member 115 may be positioned at a vertex portion of the catalyst portion 300 and being in contact with at least two side surfaces of the end portion of the catalyst portion 300 to fix the catalyst portion 300.

The body 100 may further include a vertical direction fixing member 116 protruding inward from a middle portion of the horizontal direction fixing member 115 and being in contact with one surface of the catalyst portion 300 to fix the catalyst portion 300.

An internal heat dissipation member 131 may be formed on the one surface of the substrate 220.

The internal heat dissipation member 131 may be formed to enclose the one surface of the substrate 220 except for the sealing portion 113 and a portion where the light source 210 is formed.

The internal heat dissipation member 131 may be formed to be inclined outward from a central portion where the light source 210 is positioned.

An external heat dissipation member 132 may be formed on an outer surface of one side of the body 100.

In another general aspect, a vehicle air conditioner includes: an air conditioning case 400 in which a space where introduced air is transferred is formed and a vent for discharging the air is formed; an evaporator 810 provided in the air conditioning case; a heater core 820 provided at a rear end of the air conditioning case in a direction in which the air flows; and the photocatalytic device 1000 provided in the air conditioning case.

The catalyst portion 300 may be provided so that a surface opposite to a surface facing the light source 210 faces an inside of the air conditioning case 400.

The photocatalytic device 1000 may be provided at a front end or a rear end of the evaporator 810.

A predetermined region of the air conditioning case 400 may be hollow, a mounting hole 420 closed by the photocatalytic device 1000 may be formed in the air conditioning case 400, and the photocatalytic device 1000 may be fixed in a manner in which a coupling member 117 formed on the body 100 is coupled to an outer surface of the air conditioning case 400.

Advantageous Effects

In the photocatalytic device and the vehicle air conditioner including the same according to various exemplary embodiments of the present invention as described above, the light source is disposed on one surface of the substrate, the electronic elements are disposed on the other surface, and the substrate is provided so that the one surface on which only the light source is disposed faces the catalyst portion, such that it is possible to protect the electronic elements disposed on the other surface of the substrate from contaminants.

Further, since the other surface of the substrate is sealed by using the sealing portion formed on the body, it is possible to further protect the electronic elements disposed on the other surface of the substrate from the contaminants.

In addition, since the substrate and the connector are electrically connected to each other and physically coupled to each other, and then the substrate and the body are assembled with each other, it is possible to stably couple the substrate and the connector to each other.

BEST MODE

Hereinafter, a photocatalytic device according to a preferred exemplary embodiment of the present invention will be described in detail with reference to the accompanying drawings.

Figure 1:
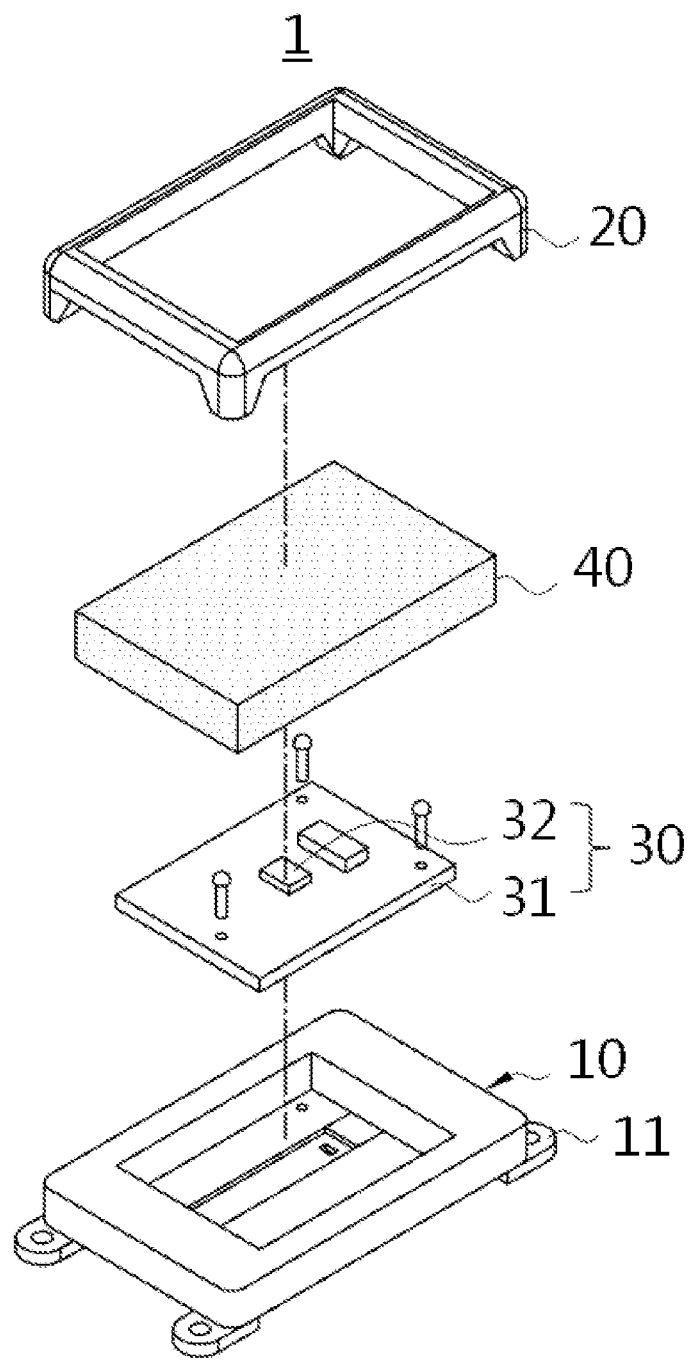
FIG. 1 is an exploded perspective view of a conventional photocatalyst filter.
Figure 2:
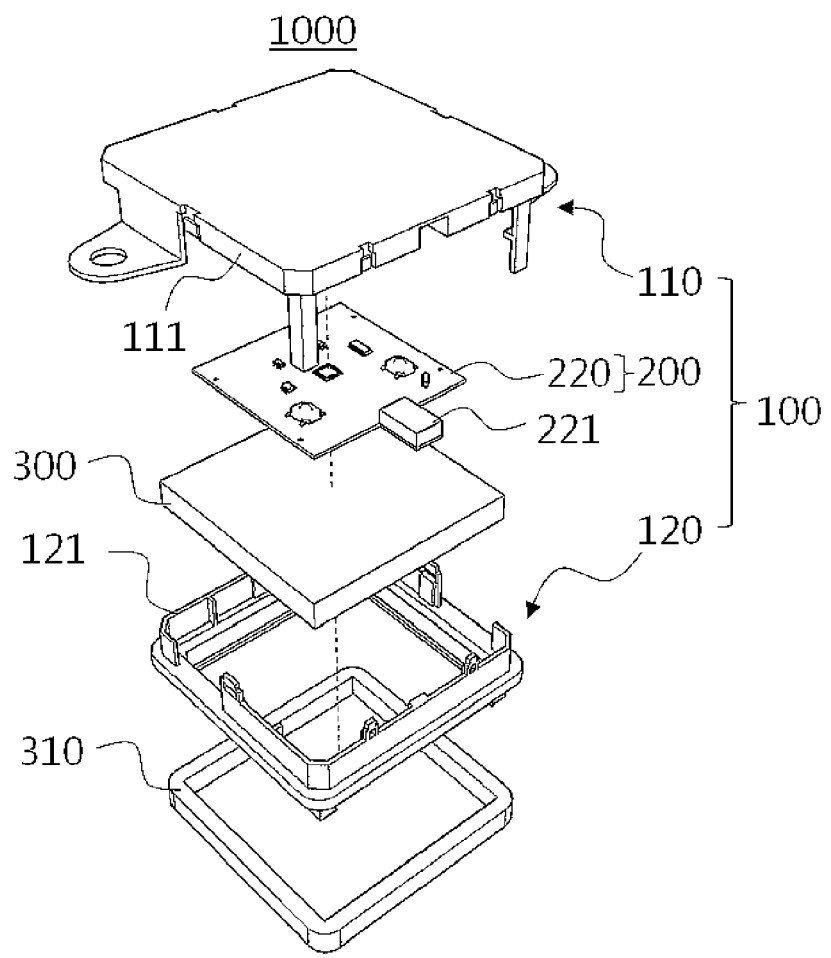
FIG. 2 is an exploded perspective view of a photocatalytic device according to an exemplary embodiment of the present invention.
Figure 3:
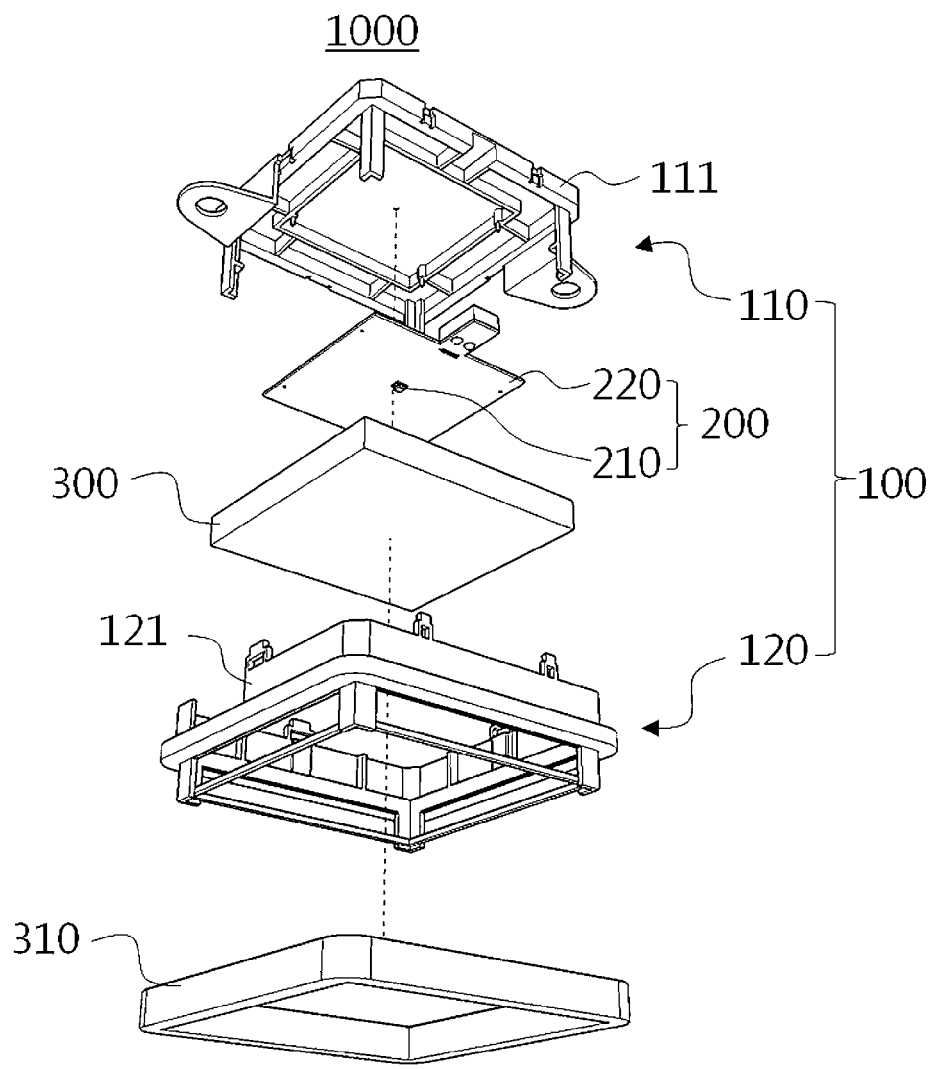
FIG. 3 is an exploded perspective view of the photocatalytic device according to the exemplary embodiment of the present invention when viewed from a different angle from that of FIG. 2.

FIG. 2 is an exploded perspective view of the photocatalytic device according to the exemplary embodiment of the present invention when viewed from above, and FIG. 3 is an exploded perspective view of the photocatalytic device according to the exemplary embodiment of the present invention when viewed from a different angle from that of FIG. 2, that is, when viewed from below.

As illustrated in FIGS. 2 and 3, the photocatalytic device according to the exemplary embodiment of the present invention may include a body 100, a light source portion 200, and a catalyst portion 300, and may further include an elastic member 310.

The body 100 is a kind of frame or housing to which the light source portion 200 and the catalyst portion 300 are fixed. The light source portion 200 and the catalyst portion 300 may be fixed to the body 100 according to the present invention in various manners. According to the exemplary embodiment of the present invention, the body 100 may include an upper body 110 and a lower body 120 coupled to each other as illustrated in FIG. 2, and the light source portion 200 and the catalyst portion 300 may be disposed and fixed between the upper body 110 and the lower body 120.

As illustrated in FIG. 2 and FIGS. 3, the upper body 110 and the lower body 120 may include an upper outer edge portion 111 and a lower outer edge portion 121, respectively, the upper outer edge portion 111 and the lower outer edge portion 121 protruding toward each other so that a space is formed in the body 100. The upper body 110 and the lower body 120 may be coupled to each other by using coupling members formed at the upper outer edge portion 111 and the lower outer edge portion 121, respectively, and corresponding to each other.

Figure 4:
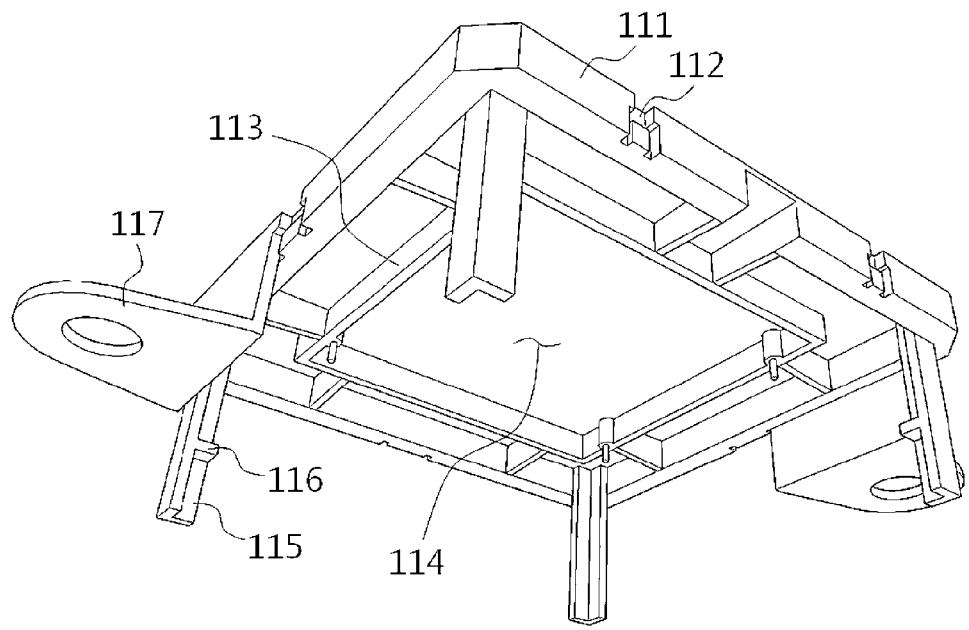
FIG. 4 is a perspective view of a lower portion of an upper body of the photocatalytic device according to the exemplary embodiment of the present invention.

FIG. 4 is an enlarged view of the upper outer edge portion 111 of FIG. 3 when viewed from below.

As illustrated in FIG. 4, an upper insertion portion 112 may be formed in an outer surface of the upper outer edge portion 111, that is, a side surface of the upper body 110, such that the coupling member formed on the lower outer edge portion 121 may be inserted thereinto. The upper insertion portion 112 has a form in which a predetermined region is recessed into the outer surface of the upper outer edge portion 111 and a part of a central portion protrudes. The coupling member of the lower outer edge portion 121 to be described later is inserted into the upper insertion portion 112.

Figure 5:
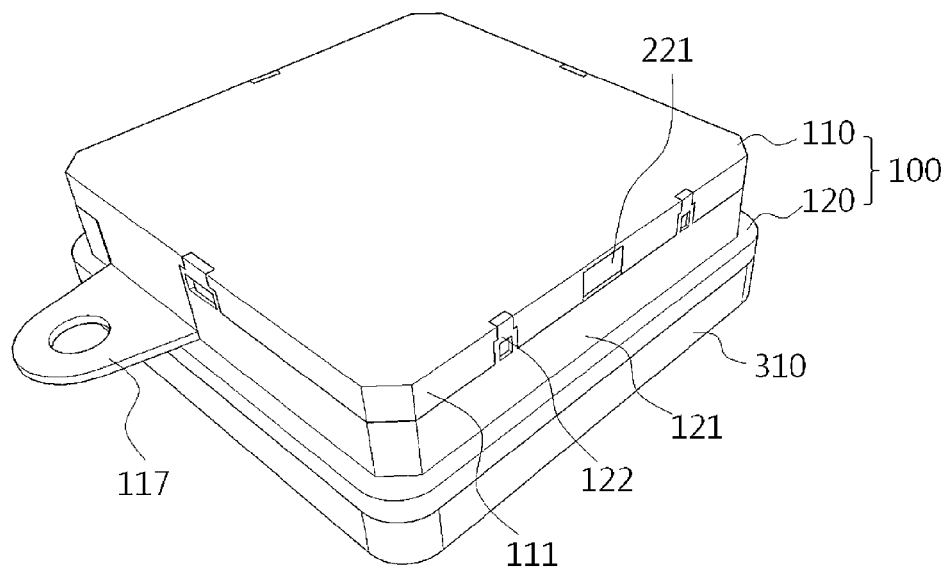
FIG. 5 is an assembled perspective view of the photocatalytic device according to the exemplary embodiment of the present invention.

FIG. 5 illustrates a state in which the upper body 110 and the lower body 120 are coupled to each other, the light source portion 200 and the catalyst portion 300 are inserted between the upper body 110 and the lower body 120, and the elastic member 310 is inserted onto a lower portion of the lower body 120.

As illustrated in FIG. 5, a lower fitting portion 122 protruding upward from the lower outer edge portion 121 of the lower body 120 is inserted into the upper insertion portion 112 to thereby couple the upper body 110 and the lower body 120 to each other. However, means for coupling the upper body 110 and the lower body 120 to each other according to the present invention is not limited to the upper insertion portion 112 and the lower fitting portion 122 described above, and the upper body 110 and the lower body 120 may be coupled to each other by using various means other than the upper insertion portion 112 and the lower fitting portion 122.

The light source portion 200 causes a photocatalytic reaction by irradiating the catalyst portion 300 with ultraviolet rays, and may include a light source 210 and a substrate 220 as illustrated in FIG. 3.

As illustrated in FIG. 3, the light source 210, which is an electronic element which emits ultraviolet rays, may be a light emitting diode (LED), but is not limited thereto. The light source 210 is formed on one surface (a lower surface in FIG. 3) of the substrate 220. Further, although one light source 210 is disposed on a lower surface of the substrate 220 in FIG. 3, the present invention is not limited thereto and a plurality of light sources 210 may be disposed and a plurality of substrates 220 may be provided.

As illustrated in FIG. 2, the substrate 220 may be a printed circuit board (PCB) for operating the light source 210, and may include an electronic element to be electrically connected to the light source 210. However, the light source 210 is positioned on the lower surface of the substrate 220 as illustrated in FIGS. 2 and 3, and various electronic elements are positioned on the other surface (an upper surface in FIGS. 2 and 3) of the substrate 220. This is to prevent damage to the electronic elements required for the substrate 220, caused by an external contamination source.

The photocatalytic device according to the exemplary embodiment of the present invention is mostly used to remove various contaminants in a flow path where gas flows. Therefore, it is likely that a contaminant included in the gas is adsorbed to the photocatalytic device, and the lower surface of the substrate 220 which is required to irradiate the catalyst portion 300 with ultraviolet rays may be easily exposed to such a contaminant. Therefore, according to the present invention, the light source portion 200 is produced in a form in which the remaining electronic elements except for the light source 210, which is required to irradiate the catalyst portion 300 with ultraviolet rays, are disposed on the upper surface of the substrate 220, thereby making it possible to protect the electronic elements of the substrate 220 from external contaminants.

Even in a case where the light source 210 is disposed on the lower surface of the substrate 220 and the electronic elements are disposed on the upper surface of the substrate 220, some contaminants may be introduced onto the upper surface where the electronic elements are positioned. In order to prevent such a problem, as illustrated in FIG. 4, the upper body 110 may include a sealing portion 113 protruding downward over the upper surface of the substrate 220 so as to be able to seal the upper surface of the substrate 220 when being coupled.

As illustrated in FIG. 4, the sealing portion 113 protrudes downward from a lower surface of the upper body 110 along an outer edge of the substrate 220 to form a sealed space 114 therein.

Figure 6:
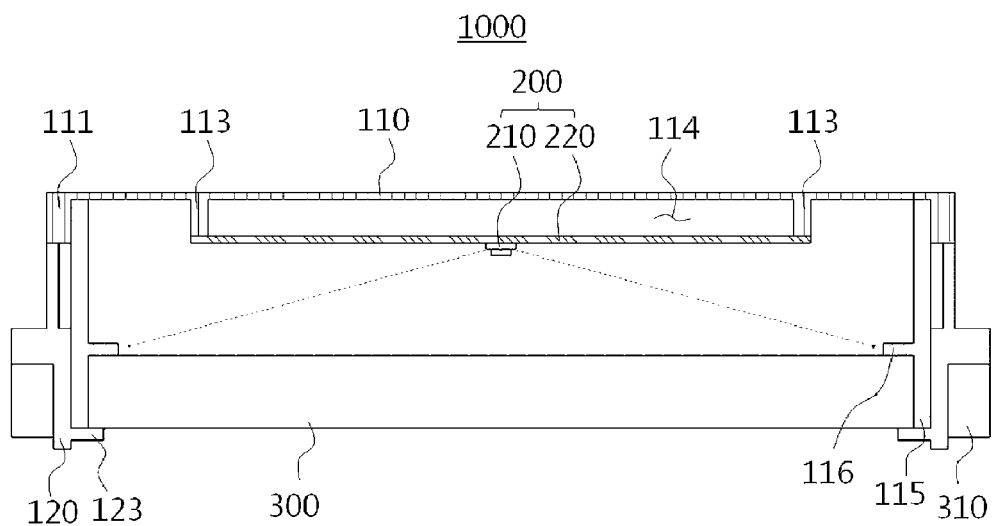
FIG. 6 is a diagonal cross-sectional view of the photocatalytic device of FIG. 5.

FIG. 6 illustrates a diagonal cross section of the photocatalytic device of FIG. 5.

As illustrated in FIG. 6, the upper surface of the substrate 220 is positioned in the sealed space 114 formed by the sealing portion 113, and thus it is possible to more efficiently prevent the various electronic elements disposed on the upper surface of the substrate 220 from being contaminated or damaged by external contaminants.

In a case where the sealing portion 113 is formed of a synthetic resin material which enables easy manufacturing of the sealing portion 113, a gap may be formed between the sealing portion 113 and the substrate 220 due to a damaged corner of the sealing portion 113, or an uneven end portion of the sealing portion 113 in a case of a defective product. In this case, gas including a contaminant may be introduced into the sealed space 114 through the gap. In the photocatalytic device according to the exemplary embodiment of the present invention, an elastic member may be inserted between a lower end of the sealing portion 113 and the substrate 220 in order to prevent the problems as described above, and the elastic member may be formed of a material such as a rubber impenetrable to gas, or a sponge material or a filter material which may separate a contaminant from the introduced gas.

As illustrated in FIG. 2, a connector 221 is formed at one side of the substrate 220. According to Prior Art 1, a method in which the connector 221 is coupled to a case such as the upper body 110, and in a case where a substrate is coupled to the case, the substrate and the connector are physically in contact with each other to be electrically connected to each other has been used. Such a method according to Prior Art 1, however, has a problem in that the substrate and the connector are physically separated from each other when the photocatalytic device shakes, such that power is not supplied to the substrate.

In the photocatalytic device according to the exemplary embodiment of the present invention, a method, in which the substrate 220 and the connector 221 are physically coupled to each other by using various methods as illustrated in FIGS. 2 and 3 and electrically connected to each other by soldering or the like, and then the substrate 220 is assembled with the upper body 110, may be used in order to prevent such a problem. The connector 221 to be connected to an external power supply needs to be partially exposed to the outside. Therefore, a separate space (no reference numeral) is formed in the upper outer edge portion 111 of the upper body 110, such that the connector 221 is positioned in the corresponding space so as to be partially exposed to the outside when the substrate 220 is assembled with the upper body 110.

The catalyst portion 300 is fixed to the body 100 and produces the photocatalytic reaction by the light emitted from the light source 210 to produce a hydroxyl radical. More specifically, once the catalyst portion 300 absorbs the light emitted from the light source 210, electrons and holes are formed on a surface of the catalyst portion 300.

The formed electron reacts with oxygen on the surface of the catalyst portion 300 to produce a hydroxyl anion and the hole reacts with moisture present in the air to produce a hydroxyl radical (neutral OH). The produced hydroxyl radical has a strong oxidizing power to decompose an odorous substance, virus, bacteria, and the like present in the air into water and carbon dioxide.

As the catalyst portion 300, titanium dioxide ($TiO_2$) which does not change by itself even when being illuminated with light and has excellent durability and wear resistance may be used. However, the present invention is not limited thereto and zinc oxide (ZnO), zirconium dioxide ($ZrO_2$), tungsten trioxide ($WO_3$), a perovskite-type composite metal oxide, or the like may be used.

As illustrated in FIG. 6, the catalyst portion 300 may be disposed to be spaced apart from the light source 210 by a predetermined distance. This is because the catalyst portion 300 may be damaged by heat depending on a material thereof in a case where heat is generated from the light source 210, and an upper surface of the catalyst portion 300 may be evenly irradiated with light in a case where the light source 210 emits light while being spaced apart from the catalyst portion 300 by a predetermined distance.

Since a position of the catalyst portion 300 may be changed by an external impact or vibration, there is a need to fix a horizontal and vertical position of the catalyst portion 300.

To this end, in the photocatalyst filter according to the exemplary embodiment of the present invention, the lower body 120 includes a lower support 123 protruding inward at the lower portion of the lower body 120 as illustrated in FIG. 6, and downward movement of the catalyst portion 300 is restricted by the lower support 123.

Further, the upper body 110 further includes a horizontal direction fixing member 115 extending downward from the lower surface of the upper body 110, and a side surface of an end portion of the catalyst portion 300 is in contact with the horizontal direction fixing member 115, such that movement of the catalyst portion 300 in a horizontal direction is restricted.

According to the exemplary embodiment of the present invention illustrated in FIG. 4, four horizontal direction fixing members 115 are formed and each enclose two different end portions at a vertex portion of the catalyst portion 300 having a rectangular shape, thereby fixing the catalyst portion 300. However, the present invention is not limited thereto and the horizontal direction fixing member 115 may have any shape as long as it encloses the side surface of the end portion of the catalyst portion 300.

The upper body 110 may further include a vertical direction fixing member 116 extending inward at a middle portion of the horizontal direction fixing member 115. The vertical direction fixing member 116 may press the upper surface of the catalyst portion 300 when the upper body 110 and the lower body 120 are coupled to each other to restrict upward movement of the catalyst portion 300.

The elastic member 310 is used when the photocatalytic device according to the exemplary embodiment of the present invention is installed in a vehicle air conditioner to be described later. The elastic member 310 is inserted onto the lower portion of the lower body 120 as illustrated in FIGS. 2, 3, and 5, and may be formed of a material with an elastic force, such as a sponge, rubber, or silicone.

As illustrated in FIG. 6, since the upper surface of the substrate 220 is sealed by the sealing portion 113 in the photocatalytic device according to the exemplary embodiment of the present invention, excessive heat may be generated. In order to prevent the generation of the excessive heat, the photocatalytic device according to the exemplary embodiment of the present invention may further include a heat dissipation member as illustrated in FIG. 7.

More specifically, an internal heat dissipation member 131 may be formed on the lower surface of the substrate 220. The internal heat dissipation member 131 is in surface-contact with the substrate 220 and encloses the sealing portion 113 to transfer heat generated from the substrate 121 to the outside. Further, the internal heat dissipation member 131 may be formed to be inclined outward from a central portion of the substrate 220 where the light source 210 is positioned while enclosing one surface of the substrate 220 except for a portion where the light source 210 is formed, and the sealing portion 113 as illustrated in FIG. 7, and this is to prevent the sealing portion 113 from blocking the light generated from the light source 210.

Figure 7:
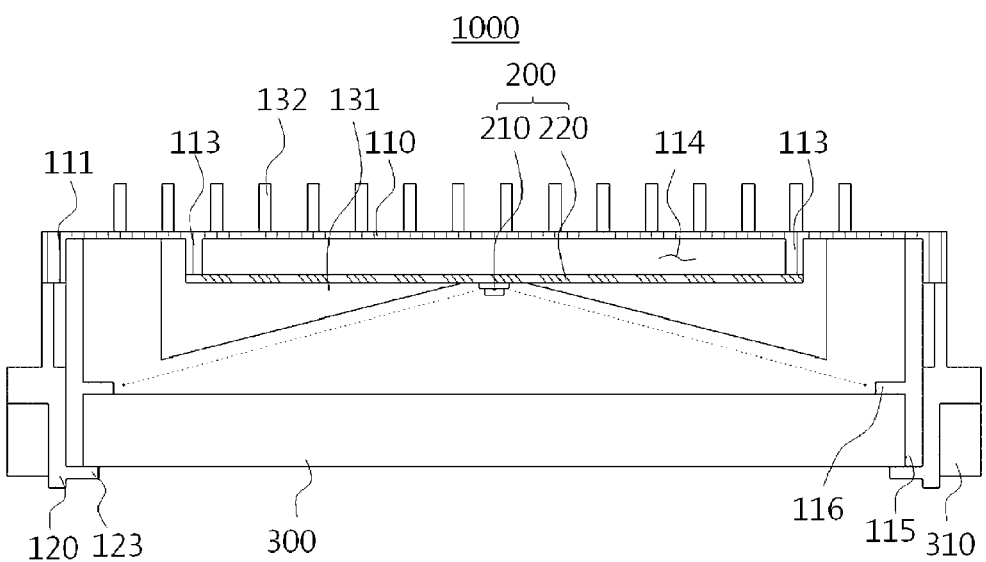
FIG. 7 is a cross-sectional view of the photocatalytic device according to the exemplary embodiment of the present invention with heat dissipation members added.

As illustrated in FIG. 7, an external heat dissipation member 132 may be formed on an upper portion of the upper body 110 to dissipate heat generated from the substrate 220. Although not illustrated in FIG. 7, the internal heat dissipation member 131 and the external heat dissipation member 132 may be connected to each other through a penetrated portion of the upper body 110 to transfer the heat generated from the internal heat dissipation member 131 to the external heat dissipation member 132.

The internal and external heat dissipation members 131 and 132 may be formed of a material with a high heat conductivity and aluminum may be typically used as the material.

[Vehicle Air Conditioner Including Photocatalytic Device]

Hereinafter, a vehicle air conditioner including the photocatalytic device according to the exemplary embodiment of the present invention will be described in detail with reference to the accompanying drawings.

Figure 8:
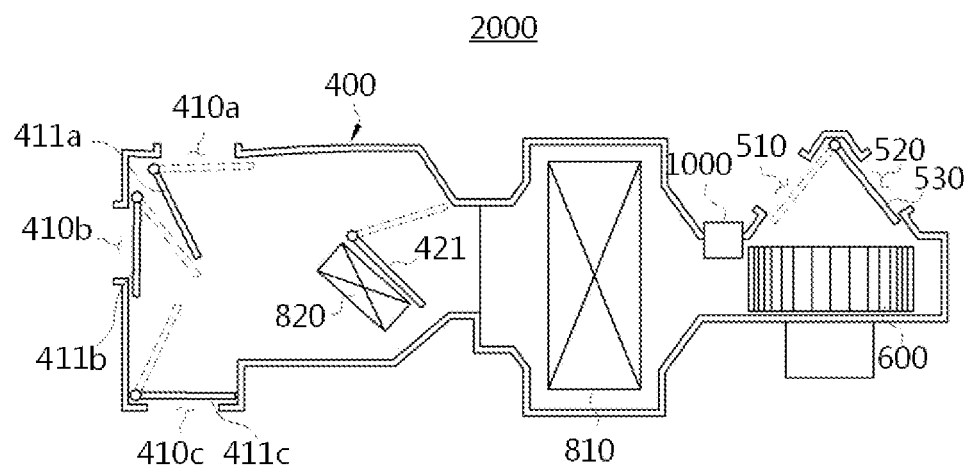
FIGS. 8 and 9 are schematic cross-sectional views of a vehicle air conditioner including the photocatalytic device according to the exemplary embodiment of the present invention.

FIG. 8 illustrates a schematic cross section of a vehicle air conditioner 2000 including the photocatalytic device according to the exemplary embodiment of the present invention.

The vehicle air conditioner 2000 according to an exemplary embodiment of the present invention will be described briefly with reference to FIG. 8. As illustrated in FIG. 8, the vehicle air conditioner 2000 including the photocatalytic device according to the exemplary embodiment of the present invention is configured in a form in which various devices are provided in an air conditioning case 400. An indoor air inlet 510 and an outdoor air inlet 520 are formed at one side of the air conditioning case 400, and a blower fan 600 is provided near the indoor air inlet 510 and the outdoor air inlet 520. Indoor air or outdoor air flows into the air conditioning case 400 and then flows from one side to the other side (from the right to the left in FIG. 8) by the blower fan 600. The indoor air or the outdoor air introduced into the air conditioning case 400 may be determined by an operation of an indoor/outdoor air switching door 530.

The air introduced into the air conditioning case 400 is discharged to vents 410a, 410b, and 410c positioned at the left side through an evaporator 810, and a discharge temperature may be adjusted by adjusting an amount of air passing through a heater core 820 and discharged to the vents, according to an operation of a temperature adjusting door 421. Mode doors 411a, 411b, and 411c which may control opening and closing of the vents are formed on the vents 410a, 410b, and 410c formed at a rear end of the air conditioning case 400, respectively, such that a location where the air is to be discharged may be selected.

Since the evaporator 810 decreases a temperature of the air introduced from a front end thereof, water may be formed and thus an odor may be produced. The photocatalytic device 1000 described above may be disposed at the front end of the evaporator 810 to absorb the odor or purify the air by sterilizing and deodorizing the evaporator 810.

Figure 9:
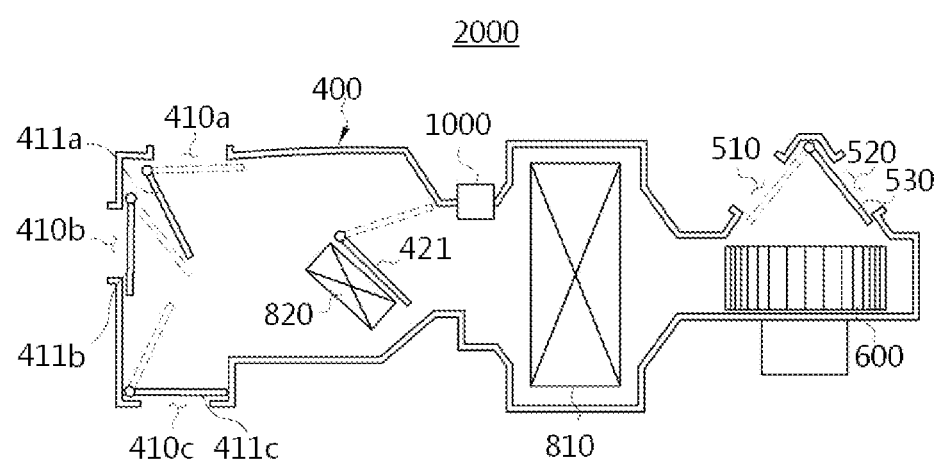

Further, the photocatalytic device 1000 may not only be provided at the front end of the evaporator 810, but also be provided at a rear end of the evaporator 810 as illustrated in FIG. 9 to sterilize and deodorize the evaporator 810 to some degrees. Further, the hydroxyl radical produced in the photocatalytic device 1000 is introduced into the interior of the vehicle, such that an effect of purifying the air in the interior of the vehicle may be expected.

Figure 10:
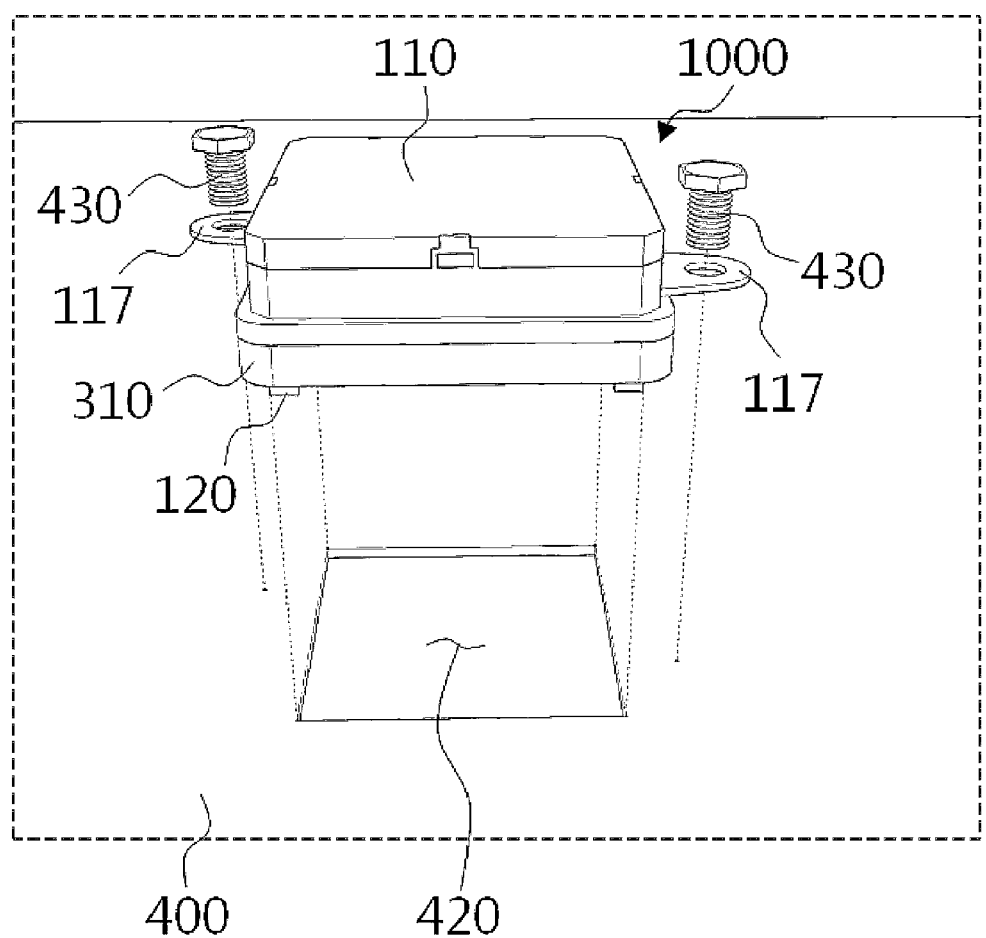
FIG. 10 is a partial perspective view of the photocatalytic device according to the exemplary embodiment of the present invention and the vehicle air conditioner.

FIG. 10 illustrates that the photocatalyst device 1000 is coupled to the air conditioning case 400.

As illustrated in FIG. 10, the air conditioning case 400 has a mounting hole 420 formed in an outer surface thereof, and the photocatalytic device 1000 may be coupled so that the photocatalytic device 1000 closes the mounting hole 420 and the lower surface (the surface that does not face the light source 210) of the catalyst portion 300 faces the inside of the air conditioning case 400.

Once the lower end of the lower body 110 of the photocatalytic device 1000 is inserted into the mounting hole 420, the elastic member 310 is compressed, and a bolt 430 is inserted into a coupling member 117 formed on the upper body 110 to couple the photocatalytic device 100 and close the mounting hole 420.

In a case where the photocatalytic device 1000 is coupled to the air conditioning case 400 while closing the mounting hole 420 as described above, since the photocatalytic device 1000 protrudes to the outside from the air conditioning case 400, inspection, repair, and replacement become easy and it is possible to minimize interference of the photocatalytic device 1000 with an air flow in the air conditioning case 400, which is advantageous.

The present invention is not limited to the abovementioned exemplary embodiments, but may be variously applied, and may be variously modified without departing from the gist of the present invention claimed in the claims.

first surface to which the light source is fixed and a second surface on which electronic elements are disposed; and a catalyst portion fixed to the body to face the light source and producing a photocatalytic reaction by light emitted from the light source to generate a superoxide radical;

wherein the substrate includes a connector formed at one side of the second surface of the substrate and fixed, wherein the connector is electrically connected to the substrate, wherein the substrate is fixed to the body, wherein the body includes an upper body and a lower body coupled to each other, in the upper body, a space is formed in a portion where the connector is positioned so that the connector is supported by the upper body, and the light source portion and the catalyst portion are positioned between the upper body and the lower body.

2. The photocatalytic device of claim 1, wherein the body includes a sealing portion protruding from a surface of the body facing the light source portion toward the light source portion.

3. The photocatalytic device of claim 2, wherein the sealing portion protrudes along an outer edge of the substrate.

4. The photocatalytic device of claim 2, wherein an internal heat dissipation member is formed on the first surface of the substrate.

5. The photocatalytic device of claim 4, wherein the internal heat dissipation member is formed to enclose the surface of the substrate except for the sealing portion and a portion where the light source is formed.

6. The photocatalytic device of claim 5, wherein the internal heat dissipation member is formed to be inclined outward from a central portion where the light source is positioned.

| [Detailed Description of Main Elements] | |
|---|---|
| 1: Photocatalyst filter | 10: First case |
| 11: Fixing member | 20: Second case |
| 100: Body | 110: Upper body |
| 111: Upper outer edge portion | 112: Upper insertion portion |
| 113: Sealing portion | 114: Sealed space |
| 115: Horizontal direction fixing member | 116: Vertical direction fixing member |
| 117: Coupling member | |
| 120: Lower body | 121: Lower outer edge portion |
| 122: Lower fitting portion | 123: Lower support |
| 131: Internal heat dissipation member | 132: External heat dissipation member |
| 200: Light source portion | 210: Light source |
| 220: Substrate | 221: Connector |
| 300: Catalyst portion | 310: Elastic member |
| 400: Air conditioning case | |
| 410a, 410b, 410c: Vent | 411a, 411b, 411c: Mode door |
| 420: Mounting hole | |
| 421: temperature adjusting door | 430: Bolt |
| 510: Indoor air inlet | 520: Outdoor air inlet |
| 530: Indoor/outdoor air switching door | |
| 600: Blower fan | |
| 810: Evaporator | 820: Heater core |
| 1000: Photocatalytic device | |
| 2000: Vehicle air conditioner including photocatalytic device | |

The invention claimed is:

1. A photocatalytic device comprising:

a body;

a light source portion including a light source and a substrate and fixed to the body, the substrate having a

7. The photocatalytic device of claim 2, wherein an external heat dissipation member is formed on an outer surface of one side of the body.

8. The photocatalytic device of claim 1, wherein the body includes a horizontal direction fixing member protruding from a surface of the body facing the catalyst portion toward the catalyst portion and contacts a side surface of an end portion of the catalyst portion to fix the catalyst portion.

9. The photocatalytic device of claim 8, wherein the catalyst portion is formed to have a polygonal shape, and the horizontal direction fixing member is positioned at a vertex portion of the catalyst portion and being in contact with at least two side surfaces of the end portion of the catalyst portion to fix the catalyst portion.

10. The photocatalytic device of claim 8, wherein the body further includes a vertical direction fixing member protruding inward from a middle portion of the horizontal direction fixing member and being in contact with a surface of the catalyst portion to fix the catalyst portion.

11. A vehicle air conditioner comprising:
an air conditioning case in which a space where introduced air is transferred is formed and a vent for discharging the air is formed;
an evaporator provided in the air conditioning case; a heater core provided at a rear end of the air conditioning case in a direction in which the air flows; and
the photocatalytic device of claim 1 provided in the air conditioning case.

12. The vehicle air conditioner of claim 11, wherein the catalyst portion is provided so that a surface opposite to a surface facing the light source faces an inside of the air conditioning case.

13. The vehicle air conditioner of claim 11, wherein the photocatalytic device is provided at a front end or a rear end of the evaporator.

14. The vehicle air conditioner of claim 11, wherein a predetermined region of the air conditioning case is hollow, a mounting hole closed by the photocatalytic device is formed in the air conditioning case, and the photocatalytic device is fixed in a manner in which a coupling member formed on the body is coupled to an outer surface of the air conditioning case.

15. A vehicle air conditioner comprising:
an air conditioning case in which a space where introduced air is transferred is formed and a vent for discharging the air is formed;
an evaporator provided in the air conditioning case; a heater core provided at a rear end of the air conditioning case in a direction in which the air flows; and
the photocatalytic device of claim 1 provided in the air conditioning case.

16. A vehicle air conditioner comprising:
an air conditioning case in which a space where introduced air is transferred is formed and a vent for discharging the air is formed;
an evaporator provided in the air conditioning case; a heater core provided at a rear end of the air conditioning case in a direction in which the air flows; and
the photocatalytic device of claim 2 provided in the air conditioning case.

17. A vehicle air conditioner comprising:
an air conditioning case in which a space where introduced air is transferred is formed and a vent for discharging the air is formed;
an evaporator provided in the air conditioning case; a heater core provided at a rear end of the air conditioning case in a direction in which the air flows; and
the photocatalytic device of claim 3 provided in the air conditioning case.

18. A photocatalytic device comprising:
A body;
A light source portion including a light source and a substrate having a first surface and a second surface, and fixed to the body, wherein the light source is fixed to the first surface and electronic elements are disposed on the second surface; and
A catalyst portion fixed to the body to face the light source and producing a photocatalytic reaction by light emitted from the light source to generate a superoxide radical;
Wherein the body includes a sealing portion protruding from a surface of the body facing the light source portion toward the light source portion,
Wherein an internal heat dissipation member is formed on the first surface of the substrate,
Wherein the internal heat dissipation member is formed to enclose the surface of the substrate except for the sealing portion and a portion where the light source is formed, and
Wherein the internal heat dissipation member is formed to be inclined outward from a central portion where the light source is positioned.

* * * * *